(12) United States Patent
Donnelly et al.

(10) Patent No.: US 11,904,111 B2
(45) Date of Patent: Feb. 20, 2024

(54) FEMALE CATHETER LOCATOR TIP

(71) Applicant: CONVATEC LIMITED, Flintshire (GB)

(72) Inventors: David A. Donnelly, Flintshire (GB); Julie Lambrethsen, Flintshire (GB); Melanie Clutton, Flintshire (GB)

(73) Assignee: ConvaTec Limited, Flintshire (GB)

(*) Notice: Subject to any disclaimer, the term of this patent is extended or adjusted under 35 U.S.C. 154(b) by 653 days.

(21) Appl. No.: 16/956,096

(22) PCT Filed: Dec. 21, 2018

(86) PCT No.: PCT/IB2018/001540
§ 371 (c)(1),
(2) Date: Jun. 19, 2020

(87) PCT Pub. No.: WO2019/123004
PCT Pub. Date: Jun. 27, 2019

(65) Prior Publication Data
US 2021/0100979 A1    Apr. 8, 2021

Related U.S. Application Data

(60) Provisional application No. 62/610,100, filed on Dec. 22, 2017.

(30) Foreign Application Priority Data

Dec. 27, 2017 (GB) ...................................... 1721956

(51) Int. Cl.
*A61M 25/01* (2006.01)
*A61M 25/00* (2006.01)

(52) U.S. Cl.
CPC .... *A61M 25/0113* (2013.01); *A61M 25/0067* (2013.01); *A61M 25/0111* (2013.01); *A61M 2210/1092* (2013.01)

(58) Field of Classification Search
CPC .. A61M 2210/1092; A61M 2210/1089; A61M 2210/1096; A61M 25/0067; A61M 25/0111; A61M 25/0113; A61M 27/00
See application file for complete search history.

(56) References Cited

U.S. PATENT DOCUMENTS 3,592,192 A * 7/1971 Harautuneian ....... A61M 25/02
604/165.01
3,709,223 A * 1/1973 Macalalad ......... A61M 25/0111
604/162

(Continued)

FOREIGN PATENT DOCUMENTS

CN    107185099 A    9/2017
DE    2509063 A1     9/1976

(Continued)

OTHER PUBLICATIONS

US 11,433,217 B2, 09/2022, Erbey, II et al. (withdrawn)

(Continued)

*Primary Examiner* — Quynh-Nhu H. Vu
(74) *Attorney, Agent, or Firm* — Taft Stettinius & Hollister LLP; Ryan O. White; Derek B. Lavender

(57) ABSTRACT

Disclosed herein are catheter assemblies (100) with a locator tip (134) proximal to the distal tip (112) of a catheter tube (110). The locator tip is sized to remain outside a female urethra and configured to allow the catheter tube to pass there through. As an example, the locator tip allows a woman using a urinary catheter to target her urethra without exposing the catheter tube to tissue until the urethra is located and insertion is initiated. This avoids infecting the urethra with a catheter tube that has been contaminated by bacteria around the urethra.

20 Claims, 6 Drawing Sheets

(56) References Cited

U.S. PATENT DOCUMENTS

| | | | |
|---|---|---|---|
| 3,750,875 A * | 8/1973 | Juster | A61M 25/002 206/484 |
| 3,854,483 A * | 12/1974 | Powers | A61M 25/0111 206/364 |
| 3,894,540 A * | 7/1975 | Bonner, Jr. | A61M 25/0111 604/171 |
| 3,898,993 A * | 8/1975 | Taniguchi | A61M 25/0111 604/172 |
| 3,934,721 A * | 1/1976 | Juster | A61M 25/002 206/364 |
| 4,652,259 A * | 3/1987 | O'Neil | A61M 25/0111 600/581 |
| 4,811,847 A * | 3/1989 | Reif | A61B 42/40 206/278 |
| 5,417,326 A * | 5/1995 | Winer | A61M 5/002 220/296 |
| 7,886,907 B2 * | 2/2011 | Murray | A61M 25/0111 604/265 |
| 8,230,993 B2 * | 7/2012 | Tanghoej | A61M 25/002 206/364 |
| 8,328,792 B2 * | 12/2012 | Nishtala | A61M 25/0017 604/317 |
| 8,758,329 B2 | 6/2014 | Paulen et al. | |
| 9,033,149 B2 * | 5/2015 | Terry | A61F 2/042 604/172 |
| 9,168,354 B2 * | 10/2015 | Hannon | A61M 25/002 |
| 9,669,187 B2 * | 6/2017 | Tjassens | A61M 25/002 |
| 10,207,076 B2 | 2/2019 | Foley et al. | |
| 10,426,584 B2 | 10/2019 | McClurg | |
| 10,426,654 B2 | 10/2019 | Ugarte | |
| 10,426,918 B2 | 10/2019 | Foley et al. | |
| 10,426,919 B2 | 10/2019 | Erbey, II et al. | |
| 10,434,282 B2 | 10/2019 | Kearns et al. | |
| 10,441,454 B2 | 10/2019 | Tanghoej et al. | |
| 10,449,083 B2 | 10/2019 | Pierson | |
| 10,449,327 B2 | 10/2019 | Overtoom | |
| 10,449,328 B2 | 10/2019 | Tanghoej et al. | |
| 10,449,329 B2 | 10/2019 | Foley et al. | |
| 10,463,466 B2 | 11/2019 | Cullison | |
| 10,463,833 B2 | 11/2019 | Clarke et al. | |
| 10,470,861 B2 | 11/2019 | Khamis et al. | |
| 10,485,483 B1 | 11/2019 | Brody | |
| 10,485,644 B2 | 11/2019 | Orr et al. | |
| 10,493,230 B2 | 12/2019 | Guldager et al. | |
| 10,493,231 B2 | 12/2019 | McMenamin et al. | |
| 10,493,252 B2 | 12/2019 | Browne et al. | |
| 10,506,965 B2 | 12/2019 | Cooper et al. | |
| 10,512,713 B2 | 12/2019 | Erbey, II et al. | |
| 10,531,894 B2 | 1/2020 | Connors et al. | |
| 10,531,976 B2 | 1/2020 | Palmer | |
| 10,548,523 B2 | 2/2020 | Ahmadi et al. | |
| 10,569,046 B2 | 2/2020 | Steindahl et al. | |
| 10,569,047 B2 | 2/2020 | Farrell et al. | |
| 10,569,051 B2 | 2/2020 | Conway et al. | |
| 10,575,935 B2 | 3/2020 | Wei et al. | |
| 10,588,774 B2 | 3/2020 | Alhaqqan | |
| 10,589,061 B2 | 3/2020 | Palmer | |
| 10,589,093 B2 | 3/2020 | Imran | |
| 10,610,344 B2 | 4/2020 | Shapiro et al. | |
| 10,610,664 B2 | 4/2020 | Erbey, II et al. | |
| 10,617,843 B2 | 4/2020 | Paz | |
| 10,631,788 B2 | 4/2020 | Brody | |
| 10,639,451 B2 | 5/2020 | Kearns et al. | |
| 10,639,452 B2 | 5/2020 | Linares et al. | |
| 10,646,688 B2 | 5/2020 | Hannon et al. | |
| 10,667,894 B2 | 6/2020 | Forsell | |
| 10,668,249 B2 | 6/2020 | Douglas et al. | |
| 10,675,134 B2 | 6/2020 | Herrera et al. | |
| 10,675,435 B2 | 6/2020 | Herrera et al. | |
| 10,682,214 B2 | 6/2020 | Sufyan et al. | |
| 10,690,655 B2 | 6/2020 | Duval | |
| 10,702,671 B2 | 7/2020 | Terry | |
| 10,709,819 B2 | 7/2020 | Littleton et al. | |
| D893,706 S | 8/2020 | Lessmann | |
| 10,736,491 B2 | 8/2020 | Truckai | |
| 10,737,057 B1 | 8/2020 | Mikhail et al. | |
| 10,744,298 B1 | 8/2020 | Bello et al. | |
| 10,751,493 B2 | 8/2020 | Gregory et al. | |
| 10,758,704 B2 | 9/2020 | Hickmott et al. | |
| 10,765,833 B2 | 9/2020 | Kearns | |
| 10,765,834 B2 | 9/2020 | Erbey, II et al. | |
| 10,772,755 B2 | 9/2020 | Gregory | |
| 10,780,243 B2 | 9/2020 | Reyes | |
| 10,780,244 B2 | 9/2020 | Conway et al. | |
| 10,780,245 B2 | 9/2020 | Schonfeldt | |
| 10,799,687 B1 | 10/2020 | Scott | |
| 10,807,287 B2 | 10/2020 | Rolsted et al. | |
| 10,814,097 B2 | 10/2020 | Palmer | |
| 11,400,257 B2 | 8/2022 | Tierney et al. | |
| 11,458,283 B2 | 10/2022 | Fletter et al. | |
| 11,666,730 B2 * | 6/2023 | Ryan | A61M 25/002 206/364 |
| 2003/0018293 A1 | 1/2003 | Tanghoj et al. | |
| 2005/0043715 A1 | 2/2005 | Nestenborg et al. | |
| 2006/0163097 A1 | 7/2006 | Murray et al. | |
| 2007/0225649 A1 * | 9/2007 | House | A61M 25/002 604/171 |
| 2009/0054876 A1 * | 2/2009 | Borodulin | A61M 25/002 604/544 |
| 2009/0137985 A1 | 5/2009 | Tanghoej et al. | |
| 2010/0324535 A1 | 12/2010 | Triel | |
| 2010/0324540 A1 | 12/2010 | Paulen et al. | |
| 2011/0184386 A1 * | 7/2011 | House | A61M 25/0111 29/460 |
| 2011/0190736 A1 | 8/2011 | Young et al. | |
| 2011/0224653 A1 | 9/2011 | Torstensen | |
| 2013/0138135 A1 | 5/2013 | Rosen et al. | |
| 2013/0161208 A1 | 6/2013 | Gustavsson | |
| 2013/0161227 A1 | 6/2013 | Gustavsson | |
| 2013/0261608 A1 | 10/2013 | Tanghoj | |
| 2013/0292286 A1 * | 11/2013 | Van Groningen | A61M 25/0111 53/425 |
| 2014/0066905 A1 | 3/2014 | Young | |
| 2014/0288517 A1 | 9/2014 | Tsai et al. | |
| 2014/0336569 A1 | 11/2014 | Gobel | |
| 2014/0378951 A1 | 12/2014 | Dye | |
| 2015/0133898 A1 | 5/2015 | Murray et al. | |
| 2015/0273180 A1 | 10/2015 | Schonfeldt | |
| 2015/0273747 A1 | 10/2015 | Montes de Oca Balderas et al. | |
| 2015/0290421 A1 | 10/2015 | Glickman et al. | |
| 2015/0297862 A1 | 10/2015 | Sadik et al. | |
| 2015/0320970 A1 | 11/2015 | Foley et al. | |
| 2016/0067445 A1 | 3/2016 | Murray et al. | |
| 2016/0184551 A1 | 6/2016 | Nyman et al. | |
| 2016/0206469 A1 | 7/2016 | Prezelin | |
| 2016/0287759 A1 | 10/2016 | Clarke et al. | |
| 2016/0317715 A1 | 11/2016 | Rostami et al. | |
| 2016/0325903 A1 | 11/2016 | Doerschner et al. | |
| 2017/0000978 A1 * | 1/2017 | Murray | A61M 25/002 |
| 2017/0021128 A1 | 1/2017 | Erbey, II et al. | |
| 2017/0056622 A1 * | 3/2017 | O'Flynn | A61M 25/0017 |
| 2017/0105826 A1 | 4/2017 | Erikstrup | |
| 2017/0348137 A1 | 12/2017 | Hvid et al. | |
| 2017/0348138 A1 | 12/2017 | Hvid et al. | |
| 2018/0015250 A1 | 1/2018 | Tsukada et al. | |
| 2018/0021481 A1 | 1/2018 | Yin et al. | |
| 2018/0050173 A1 | 2/2018 | Kearns | |
| 2018/0071482 A1 | 3/2018 | Fitzpatrick et al. | |
| 2018/0193618 A1 | 7/2018 | Erbey et al. | |
| 2018/0326179 A1 | 11/2018 | Erbey et al. | |
| 2018/0369474 A1 | 12/2018 | Falleboe et al. | |
| 2019/0099583 A1 | 4/2019 | Charlez et al. | |
| 2019/0126004 A1 * | 5/2019 | O'Brien | A61M 25/002 |
| 2019/0224402 A1 | 7/2019 | Henry et al. | |
| 2019/0240060 A1 | 8/2019 | He et al. | |
| 2019/0247549 A1 | 8/2019 | Nielsen | |
| 2019/0314044 A1 | 10/2019 | Long et al. | |
| 2019/0314188 A1 | 10/2019 | Barrientos | |
| 2019/0314190 A1 | 10/2019 | Sanchez et al. | |
| 2019/0321587 A1 | 10/2019 | McMenamin et al. | |
| 2019/0321589 A1 | 10/2019 | Bonneau | |
| 2019/0358075 A1 | 11/2019 | Scharich et al. | |

(56) References Cited

U.S. PATENT DOCUMENTS

| | | |
|---|---|---|
| 2019/0358435 A1 | 11/2019 | Andersin et al. |
| 2019/0365561 A1 | 12/2019 | Newton et al. |
| 2019/0366038 A1 | 12/2019 | Denman et al. |
| 2019/0374324 A1 | 12/2019 | Luleci |
| 2019/0381291 A1 | 12/2019 | Feld |
| 2019/0388659 A1 | 12/2019 | Ruel |
| 2020/0001045 A1 | 1/2020 | McIntyre |
| 2020/0001049 A1 | 1/2020 | House |
| 2020/0016380 A1 | 1/2020 | Murray et al. |
| 2020/0022636 A1 | 1/2020 | Suehara et al. |
| 2020/0030135 A1 | 1/2020 | Woodyard |
| 2020/0030582 A1 | 1/2020 | Dong |
| 2020/0030595 A1 | 1/2020 | Boukidjian et al. |
| 2020/0037832 A1 | 2/2020 | Wang et al. |
| 2020/0054800 A1 | 2/2020 | Wilbourn et al. |
| 2020/0094017 A1 | 3/2020 | Erbey, II et al. |
| 2020/0101280 A1 | 4/2020 | Peddicord |
| 2020/0129731 A1 | 4/2020 | Brar et al. |
| 2020/0139109 A1 | 5/2020 | Imran |
| 2020/0146799 A1 | 5/2020 | Connors et al. |
| 2020/0146871 A1 | 5/2020 | Palmer |
| 2020/0163543 A1 | 5/2020 | Schutt et al. |
| 2020/0163699 A1 | 5/2020 | Bacich et al. |
| 2020/0179644 A1 | 6/2020 | Guldbaek |
| 2020/0179665 A1 | 6/2020 | Orr et al. |
| 2020/0188631 A1 | 6/2020 | Hannon et al. |
| 2020/0206389 A1 | 7/2020 | Vange |
| 2020/0206411 A1 | 7/2020 | Henry et al. |
| 2020/0206468 A1 | 7/2020 | Olson et al. |
| 2020/0206470 A1 | 7/2020 | Orr et al. |
| 2020/0214820 A1 | 7/2020 | Bunch et al. |
| 2020/0215303 A1 | 7/2020 | Erbey II et al. |
| 2020/0222188 A1 | 7/2020 | Smith et al. |
| 2020/0222220 A1 | 7/2020 | Kappus et al. |
| 2020/0222659 A1 | 7/2020 | Schertiger et al. |
| 2020/0222660 A1 | 7/2020 | Erbey, II et al. |
| 2020/0222674 A1 | 7/2020 | Inoue et al. |
| 2020/0229964 A1 | 7/2020 | Staali et al. |
| 2020/0230349 A1 | 7/2020 | McMenamin et al. |
| 2020/0230356 A1 | 7/2020 | Utas et al. |
| 2020/0230382 A1 | 7/2020 | Siebert |
| 2020/0238048 A1 | 7/2020 | Palmer |
| 2020/0246587 A1 | 8/2020 | Tal et al. |
| 2020/0246589 A1 | 8/2020 | Starr |
| 2020/0246594 A1 | 8/2020 | Miller |
| 2020/0254215 A1 | 8/2020 | Portela et al. |
| 2020/0261692 A1 | 8/2020 | Palmer |
| 2020/0262868 A1 | 8/2020 | Ricca et al. |
| 2020/0268947 A1 | 8/2020 | Erbey, II et al. |
| 2020/0276046 A1 | 9/2020 | Staali et al. |
| 2020/0276410 A1 | 9/2020 | Son |
| 2020/0281760 A1 | 9/2020 | Fleming |
| 2020/0282092 A1 | 9/2020 | Paul et al. |
| 2020/0306502 A1 | 10/2020 | Luning et al. |
| 2020/0315445 A1 | 10/2020 | Cheng et al. |
| 2020/0324006 A1 | 10/2020 | Paul et al. |
| 2020/0330724 A1 | 10/2020 | Mikhail et al. |
| 2020/0375781 A1 | 12/2020 | Staali et al. |
| 2021/0170149 A1 | 6/2021 | Erbey et al. |
| 2021/0290910 A1 | 9/2021 | Orr et al. |
| 2021/0361908 A1 | 11/2021 | Erbey et al. |
| 2021/0386969 A1 | 12/2021 | O'Flynn |
| 2022/0001136 A1 | 1/2022 | Hede et al. |
| 2022/0047844 A1 | 2/2022 | Gobel |
| 2022/0054798 A1 | 2/2022 | Erbey et al. |
| 2022/0118161 A1 | 4/2022 | Bager et al. |
| 2022/0184342 A1 | 6/2022 | Erbey et al. |
| 2022/0241557 A1 | 8/2022 | Erbey, II et al. |
| 2022/0362515 A1 | 11/2022 | Erbey, II et al. |

FOREIGN PATENT DOCUMENTS

| | | |
|---|---|---|
| EP | 3001976 A1 | 4/2016 |
| EP | 3100758 A1 | 12/2016 |
| EP | 3315159 A1 | 5/2018 |
| EP | 3351208 A1 | 7/2018 |
| EP | 3613457 A1 | 2/2020 |
| EP | 3727550 B1 | 10/2021 |
| EP | 3886960 A1 | 10/2021 |
| EP | 3892320 A1 | 10/2021 |
| EP | 3912669 A1 | 11/2021 |
| EP | 3921009 A1 | 12/2021 |
| EP | 3943140 A1 | 1/2022 |
| EP | 3955863 A1 | 2/2022 |
| EP | 3727549 B1 | 6/2022 |
| EP | 4005479 A1 | 6/2022 |
| GB | 2579273 A | 6/2020 |
| JP | 2020011103 A | 1/2020 |
| WO | 2004054653 A1 | 7/2004 |
| WO | 2009048375 A1 | 4/2009 |
| WO | 2009054720 A2 | 4/2009 |
| WO | 2018134591 A1 | 7/2018 |
| WO | 2018143487 A1 | 8/2018 |
| WO | 2019014344 A1 | 1/2019 |
| WO | 2019038732 A1 | 2/2019 |
| WO | 2019038734 A1 | 2/2019 |
| WO | 2019106581 A2 | 6/2019 |
| WO | 2019123004 A1 | 6/2019 |
| WO | 2019184222 A1 | 10/2019 |
| WO | 2019222644 A1 | 11/2019 |
| WO | 2019229597 A1 | 12/2019 |
| WO | 2020015804 A1 | 1/2020 |
| WO | 2020093698 A1 | 5/2020 |
| WO | 2020110046 A1 | 6/2020 |
| WO | 2020110051 A1 | 6/2020 |
| WO | 2020132731 A1 | 7/2020 |
| WO | 2020136503 A1 | 7/2020 |
| WO | 2020136645 A1 | 7/2020 |
| WO | 2020144302 A1 | 7/2020 |
| WO | 2020160738 A1 | 8/2020 |
| WO | 2020173531 A1 | 9/2020 |
| WO | 2020173942 A1 | 9/2020 |
| WO | 2020178711 A1 | 9/2020 |
| WO | 2020214944 A1 | 10/2020 |
| WO | 2021116295 A1 | 6/2021 |
| WO | 2021154686 A1 | 8/2021 |

OTHER PUBLICATIONS

US 11,433,219 B2, 09/2022, Erbey, II et al. (withdrawn)
Extended European Search Report; European Patent Office; European Patent Application No. 21197247.6; dated Dec. 6, 2021; 10 pages.

\* cited by examiner

FEMALE CATHETER LOCATOR TIP

CROSS-REFERENCE TO RELATED APPLICATIONS

This application is a national phase entry of International Application No. PCT/IB2018/001540 filed on Dec. 21, 2018 and claims the benefit of U.S. Provisional Application No. 62/610,100 filed Dec. 22, 2017, and GB 1721956.9, filed Dec. 27, 2017, each of which is incorporated by reference herein in its entirety.

BACKGROUND OF THE DISCLOSURE

Intermittent self-catheterization catheters are temporary, single-use catheters for draining urine from a bladder or surgically connected channel.

For catheters for use by a woman, some problems may be enhanced due to the location of the urethra and its proximity to the vaginal area, a particularly sensitive area. For example, aligning the catheter tip with the urethra, which is near the vaginal area, can cause a great deal of discomfort.

SUMMARY OF THE DISCLOSURE

The present disclosure provides catheters that overcome, alleviate, and mitigate the aforementioned issues and other deleterious effects. The present disclosure provides catheters that address women's anatomy by incorporating features intended to provide comfortable self-guided application. Devices, systems and components thereof, as described herein, may be useful for medical tubes, probes and guides including urinary catheters, colonoscopy probes, trachea tubes, feeding tubes, and arterial catheters. Devices, systems and components thereof, as described herein, may be useful for inserting a medical tube or guidewires into a bodily orifice that is difficult to locate due to position or circumstance.

The present disclosure provides catheter devices that allow safe and controlled handling for insertion into, for example, a body cavity or tube. In some embodiments, the intermittent catheter devices disclosed herein comprise a locator tip that assists a user with insertion into, for example, a urethral location. Intermittent catheter devices disclosed herein may reduce trauma to the vaginal area of a woman. Intermittent catheter devices disclosed herein may prevent urinary tract infections because the locator tip may prevent exposure of the catheter tube to potential contaminants present in, for example, the vaginal area up until the urethra is located and the catheter tube is inserted.

The present disclosure also provides for methods of using self-guiding locator devices provided with the disclosed intermittent catheter devices. Methods may comprise contacting tissue around the urethral opening with an intermittent catheter device in an effort to locate the urethral opening, wherein the intermittent catheter device comprises a locator tip proximal the distal end of the catheter tube, and exposing the distal end of the catheter tube to the urethra opening after the urethra opening is detected. In some instances, methods comprise substantial avoidance of the locator tip device from contacting other body structures (for example, vaginal tissue) prior to entering the urethra opening. In some instances, methods comprise pushing the catheter tube through the locator tip and into the urethra after the urethra opening is detected.

Disclosed herein, in some aspects, are catheter assemblies comprising a catheter tube having a distal tip with a catheter tube distal opening to be inserted into a urethra of a female subject and a proximal tip having at least one catheter tube proximal opening; and a locator tip located proximal the distal tip of the catheter tube, wherein the locator tip is sized to remain outside a female urethra and configured to allow the catheter tube to pass there through. In some instances, the locator tip appears conical from a side view of the catheter assembly. In some instances, the locator tip appears rounded from a side view of the catheter assembly. In some instances, the locator tip appears circular from an end view of the catheter assembly. In some instances, the locator tip is characterized by a height that is parallel with the length of the catheter tube and a width that is perpendicular to the length of the catheter tube when the catheter tube is extended. In some instances, the width is not less than 2 cm. In some instances, the width is not less than 1.5 cm. In some instances, the width is not less than 1 cm. In some instances, the height is not greater than 1 cm. In some instances, the catheter tube is located in a housing having an outer body and a cavity within the outer body, the housing having a distal end proximal the locator tip and a proximal end. In some instances, catheter assemblies comprise an actuator configured to be engaged by a user, wherein the actuator pushes the catheter tube out of the housing, through the locator tip and into the urethra. In some instances, the housing has a housing proximal opening at the proximal end, and wherein the housing proximal opening is configured to allow the actuator to move there through. In some instances, catheter assemblies comprise a sleeve, wherein the sleeve is configured to be held by the user as the urethra is being located. In some instances, catheter assemblies comprise a cap, configured to cover the locator tip until use. In some instances, the cap is also configured to cover the catheter tube proximal opening after use. In some instances, the catheter tube comprises a funnel on the proximal tip and the cap is also configured to cover the funnel after use. In some instances, catheter assemblies comprise a wetting device, wherein the wetting device is located behind the locator tip, and is configured to allow at least a portion of the catheter there through. In some instances, catheter assemblies comprise a sleeve, wherein the sleeve is connected to the locator tip. In some instances, the sleeve is compacted prior to use. In some instances, the sleeve and locator tip are compacted in a proximal region of the catheter assembly prior to use. In some instances, catheter assemblies comprise a case for storing the catheter assembly. In some instances, the locator tip is engaged or connected to the case. In some instances, upon removal of the catheter assembly from the case, the sleeve is extended over the catheter tube. In some instances, the locator tip is disengaged from the case when the distal end of the catheter assembly is removed from the case. In some instances, catheter assemblies comprise a wetting device. In some instances, the catheter tube is wetted with a wetting agent upon removal of the catheter assembly. Also disclosed herein are uses of catheter assemblies disclosed herein, comprising: probing tissue around a female urethra with the locator tip; and inserting the catheter tube into the urethra, wherein the locator tip is not inserted into the urethra.

DETAILED DESCRIPTION

Figure 1:
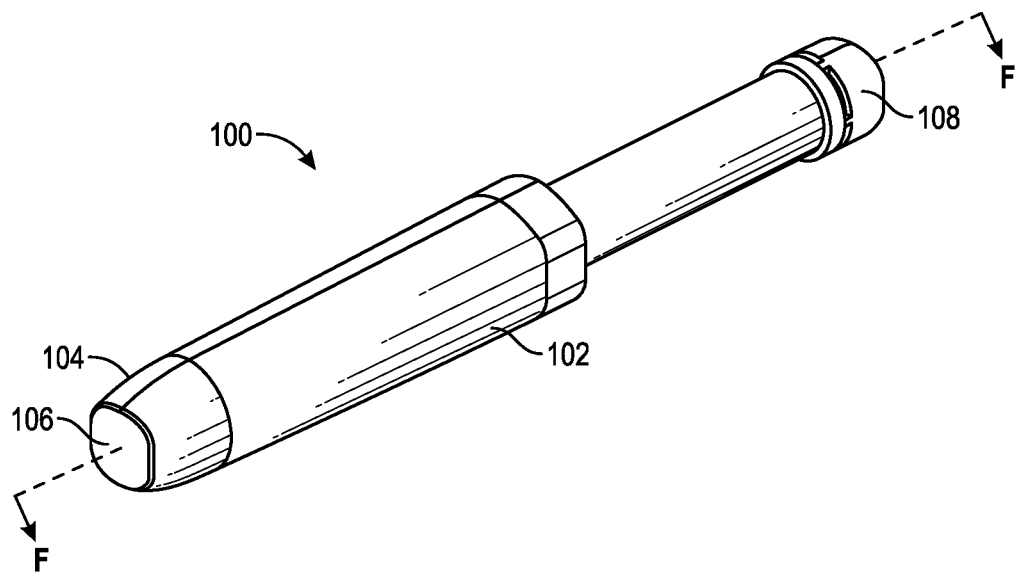
FIG. 1 shows an outer view of an exemplary female urinary catheter.

In general, it can be difficult for a female catheter user to locate her urethral opening. Some users may use a mirror to overcome the issue, but trying to locate a small opening in a mirrored image is challenging. The result is that many users end up applying trial and error application—prodding around until they find the urethral opening. For every time the catheter tip touches the tissue around the urethral opening, i.e., vaginal or rectal areas, there is a potential risk of contaminating the tip with bacteria which may be carried into the urethra/bladder upon insertion of the catheter tube. This contamination carries a risk of causing a urinary tract or kidney infection. Locator tips disclosed herein minimize or eliminate this potential contamination issue by providing self-guiding mechanisms to allow insertion of the catheter tip into the urethral opening.

Locator tips disclosed herein may prevent a catheter tube from being exposed to tissue of a subject until a urethral opening is located. The locator tip allows the user to target the meatus, moving the locator tip around the general area of the meatus until the urethral entrance has been located, thereby potentially limiting contaminating organisms to the outside of the locator tip which does not enter the urethra. Once the device is in the correct location, the catheter tube is moved distally past the locator tip and thereby applied straight into the urethra without having had any exposure to the surrounding tissue. Because of its design, the locator tip does not enter into the urethral tube but remains at or near the urethral opening, further minimizing or potentially eliminating introduction of contaminating organisms on the locator tip from entering the urethral tube. There are no compact female devices in the market today that offer such a safety feature.

Disclosed herein are catheter assemblies that comprise a catheter tube and a locator tip. Generally, the catheter tube has a distal tip with a catheter tube distal opening to be inserted into a urethra of a female subject. The catheter tube also has a proximal tip having at least one catheter tube proximal opening for the release and disposal of urine.

In general, catheter assemblies disclosed herein are configured such that the locator tip is located proximal to the distal tip of the catheter tube before use. In some instances, the locator tip is located distal to the distal tip of the catheter tube. In some instances, the locator tip covers the distal tip of the catheter tube. In some instances, the locator tip covers the distal tip of the catheter tube, but does not contact the distal tip of the catheter tube. In some instances, the locator tip covers the distal tip of the catheter tube and does contact the distal tip of the catheter tube. In some instances, there is a space between the locator tip and the distal tip of the catheter tube. The space may have a dimension as great as 2 cm. In some instances, the space's greatest dimension is less than 2 cm. In some instances, the space's greatest dimension is less than 1.8 cm. In some instances, the space's greatest dimension is less than 1.6 cm. In some instances, the space's greatest dimension is less than 1.4 cm. In some instances, the space's greatest dimension is less than 1.2 cm. In some instances, the space's greatest dimension is less than 1 cm. In some instances, there is a wetting agent between the locator tip and the distal tip of the catheter tube. In some instances, there is at least a portion of a wetting device between the locator tip and the distal tip of the catheter tube. In yet other instances, the wetting device may be located distal to the locator tip prior to use or activation.

Generally, locator tips disclosed herein are sized to remain outside a female urethra while configured to allow the catheter tube to pass therethrough. The locator tip may be characterized by a height, wherein the height is measured from the point of the locator tip closest to the distal tip of the catheter tube (also referred to as the "locator tip end") to the point of the locator tip furthest from the distal tip of the catheter tube (also referred to as the "locator tip base"). In some instances, the height is parallel with the length of the catheter tube. The height may be less than 2 cm. The height may be less than 1.7 cm. The height may be less than 1.5 cm. The height may be less than 1 cm. In some instances, the height is at least 0.2 cm. In some instances, the height is at least 0.3 cm. In some instances, the height is at least 0.4 cm. In some instances, the height is between 0.5 mm and 10 mm. In some instances, the height is between 1 mm and 10 mm. In still other instances, the height is between 2 mm and 8 mm. In yet other instances, the height is between 3 mm and 6 mm.

Locator tips disclosed herein may be characterized by a width. The width may be a diameter. The width may be the greatest distance between two points on a perimeter of the locator tip, wherein the perimeter is in a plane perpendicular to the height of the locator tip. In some instances, the width is perpendicular to the length of the catheter tube when the catheter tube is extended. The locator tip may only be slightly wider than the catheter tube in order to allow passage of the catheter through the tip. Slightly wider may be 0.5 mm to about 1 mm wider. Slightly wider may be 0.5 mm to about 2 mm wider. Slightly wider may be 1 mm wider to 3 mm wider. By way of non-limiting example, urinary catheter tubes typically vary from 2 mm to 8 mm in diameter. A locator tip inner diameter may be 3 mm to 12 mm to allow for a slight gap between the catheter tube and an inner surface of a locator tip. Locator tips disclosed herein may have an outer width or outer diameter. The outer width or outer diameter may be 0.1 cm to 1 cm. The outer width or outer diameter may be 1 cm to 2 cm. The outer width or outer diameter may be at least 0.5 cm. The outer width or outer diameter may be at least 0.1 cm. The outer width or outer diameter may be less than 1 cm. The outer width or outer diameter may be less than 2 cm. The outer width or outer diameter may be less than 0.5 cm.

Locator tips disclosed herein may be characterized by a shape or form. As viewed from the side, the locator tip may appear conical. As viewed from the slide, the locator tip may appear tapered. As viewed from the side, the outer surface of the locator tip wall may be at an angle from the plane of the circumference of the locator tip base. The angle may be about 1 degree to about 40 degrees. The angle may be about 1 degree to about 35 degrees. The angle may be about 1 degree to about 30 degrees. The angle may be about 1 degree to about 25 degrees. The angle may be about 5 degrees to about 30 degrees. The angle may be about 10 degrees to about 30 degrees. As viewed from the side, the locator tip may appear rounded. As viewed from the side, the locator tip may appear curved. As viewed from the side, the locator tip may appear convex or dome-shaped, with an apex of the dome nearest the urethra. As viewed from the side, the locator tip may appear tiered. As viewed from the side, the locator tip end may appear flat. As viewed from the side, the locator tip end may appear blunt. From a top view (looking down the length of the catheter tube from its distal tip), the locator tip may appear circular. From the top view, the locator tip may appear round. From the top view, the locator tip may appear oval-shaped. From the top view, the locator tip may appear star-shaped. From the top view, the locator tip may appear polygonal.

Locator tips disclosed herein may comprise a locator tip material that is comfortable to the subject when contacting tissue around the opening of the subject. In some instances, locator tips may include a mixture of materials that allow comfort but substantial hardness to provide a guide for locating the urethral opening without collapsing for the catheter tube to pass through. In some instances, locator tips may consist essentially of the locator tip material. In some instances, locator tips consist of the locator tip material. In some instances, the locator tip material is rubber. In some instances, the locator tip material is an elastomer. In some instances, the elastomer is a soft-touch elastomer. In some instances, the elastomer is a thermoplastic elastomer. In some instances, the locator tip material is foam. The foam may be an open cell foam. In yet other instances, the locator tip may comprise one or more of these materials.

Locator tips disclosed herein may be characterized by a Shore hardness. The Shore hardness may be 30 A to 70 A. The Shore hardness may be 20 A to 80 A. The Shore hardness may be 30 A to 90 A. The Shore hardness may be 10 A to 70 A. In some instances, the Shore hardness is 40 A to 60 A. The Shore hardness may be suitable to locator tips of a certain height. For example, the Shore hardness may be 30 A to 70 A and the tip height 3 mm to 5 mm. In some instances, the Shore hardness is 30 A to 70 A and the tip height is about 2 mm to about 6 mm. In some instances, the Shore hardness is 20 A to 80 A and the tip height is about 3 mm to about 7 mm. In some instances, the Shore hardness is 20 A to 100 A and the tip height is about 3 mm to about 10 mm. In some instances, the Shore hardness is 30 A to 90 A and the tip height is about 3 mm to about 8 mm. In some instances, the locator tip height is not more than 5 mm. In some instances, the locator tip height is at least 1 mm. In some instances, the Shore hardness is not more than 100 A. In some instances, the Shore hardness is not more than 90 A. In some instances, the Shore hardness is not more than 80 A. In some instances, the Shore hardness is at least 20 A.

Locator tips disclosed herein are generally hollow and may be described as a cylindrical wall. The cylindrical wall may have a maximum thickness. The maximum thickness may be at least about 2 mm. The maximum thickness may be at least about 1 mm. The maximum thickness may be less than 1 mm. The wall may be tapered. For example, the wall may be thinner at the distal most tip of the assembly and thicker near its base (e.g., nearer the proximal end of the assembly). In some instances, the wall thickness is 0.6 mm to 0.8 mm when measured about 4 mm from the distal most tip, 0.5 mm to 0.7 mm, when measured about 2 mm from the very tip and about 0.3 to about 0.4 mm at the very tip. The maximum wall thickness may be at least 0.3 mm. Molding restrictions may require minimal wall thickness to be at least 0.4 mm.

Locator tips disclosed herein may comprise a locator tip opening that allows a catheter tube to pass therethrough. The locator tip opening may be circular. The locator tip opening may have a diameter that is the same as that of the catheter tube. The locator tip opening may have a diameter that is smaller than that of the catheter tube. The locator tip opening may have a diameter that is larger than that of the catheter tube. The locator tip opening may be oval-shaped. The locator tip opening may be polygonal. The locator tip opening may be diamond-shaped. The locator tip opening may have a width that is the same as that of the catheter tube. The locator tip opening may have a width that is smaller than that of the catheter tube. The locator tip opening may have a width that is larger than that of the catheter tube. The locator tip opening may be a slit in the locator tip opening. The locator tip opening may comprise a slit in the locator tip opening. The locator tip opening may comprise plurality of slits in the locator tip opening. The locator tip opening may resemble an asterisk or star.

Locator tip openings, as disclosed herein, generally accommodate passage of urinary catheter tubes. However, locator tip openings disclosed herein are generally flexible due to the material of the locator tip. By way of non-limiting example, the locator tip opening may be a slit and thus, the locator tip opening is less than 1 mm wide before the urinary catheter tube passes there through, but then stretches to a width of half of a centimeter to accommodate the urinary catheter tube. Before use of the urinary catheter tube, the locator tip opening may be about 0.1 mm to about 5 mm wide. Before use of the urinary catheter tube, the locator tip opening may be about 0.1 mm to about 3 mm wide. Before use of the urinary catheter tube, the locator tip opening may be about 0.1 mm to about 1 mm wide. Before use, the locator tip opening may be about 0.5 mm to about 5 mm wide.

Locator tips disclosed herein may comprise a cover material that can be broken, torn, bent, or deformed by the catheter tube to create an opening when the catheter tube assembly is put to use. The locator tip may comprise a body, wherein the body comprises a locator tip opening located at a point of the locator tip furthest from the distal tip of the catheter tube, and the locator tip opening is covered by a cover material. By way of non-limiting example, the catheter tube comprises a soft-touch elastomer and the cover material comprises a wax lined paper. The opening material should be configured to remain connected to the locator tip even after it is modified (e.g., torn, bent) by the catheter tube to avoid introducing foreign material into the urethra. Non-limiting examples of cover materials are paper, wax, foam, plastic, metallised foil, coated foil (e.g. plastic or wax coated).

Catheter assemblies disclosed herein may comprise a housing having an outer body and a cavity within the outer body, the housing having a distal end proximal the locator tip and a proximal end. In some instances, at least a portion of the catheter tube is contained in the cavity before use. In some instances, at least a portion of the catheter tube is contained in the cavity after use. In some instances, a locator tip of the catheter assembly is located outside of the cavity. In some instances, a locator tip of the catheter assembly is located outside of the cavity. In some instances, a locator tip of the catheter assembly is located at the proximal end of the housing. In some instances, the locator tip is attached to the outer body. In some instances, the locator tip is welded to the outer body. In some instances, the locator tip is attached to the outer body by an adhesive. In some instances, the locator tip is attached to the outer body by press-fit.

Catheter assemblies disclosed herein may comprise a housing, wherein the housing comprises a cap. The cap may cover the locator tip until use. The cap may be configured to be pulled off from the housing before use. The cap may be configured to screw off of the housing before use. The cap may be configured to be pulled off from the locator tip before use. The cap may be configured to screw off of the locator tip before use. The cap may be a lid that is connected to the housing by a hinge. The cap may comprise a tamper-evident indicator. For example, the catheter assembly may comprise a tab, seal, wax, foil, adhesive or other material in connection with the cap, such that after the cap is removed, a tear, fatigue mark, or simply absence of the material reveals that the catheter tube has already been used or at least exposed. The cap may be configured to be re-attached to the housing after use. The cap may be configured to be re-attached to the housing at a different location than its location before use. By way of non-limiting example, the cap may be configured to be re-attached to the housing at its proximal end in order to cover the funnel after use. The cap may be configured to be returned to its original position after use. In some instances, catheter assemblies disclosed herein comprise at least two caps, wherein a first cap is positioned at the proximal end of the housing and the second cap is positioned at the distal end of the housing. In some instances, catheter assemblies comprise a seal that keeps fluids (e.g., urine) from leaking out of the catheter assembly after use and replacement of a cap on the housing. A non-limiting example of a seal is a rubberized or plasticized O-ring.

In some instance, catheter assemblies disclosed herein comprise a wetting device positioned proximal or distal to the locator tips disclosed herein. In some instances, the wetting device comprises a chamber defined by an enclosure having at least two apertures; and a wetting applicator having an opening, the wetting applicator disposed in the chamber with the opening between the two apertures so that as a catheter tube traverses the chamber from one body surface to the other body surface, an outer surface of the catheter tube is properly wetted by the wetting applicator. The wetting device may have a body that has a plurality of walls including a first end wall opposite a second end wall. In some instances, the at least two apertures are in axial alignment. In some instances, the wetting applicator is compressible and impregnable with the wetting agent. In some instances, the wetting applicator is loadable with a wetting agent. In some instances, the wetting device comprises a port disposed through the enclosure thereof for loading a wetting agent into the chamber. In some instances, the wetting device may comprise a connector having an axial through bore in communication with the catheter tube drainage end. The connector may span the chamber from the first end wall to the second end wall to seal the two apertures so the chamber is sealed in its pre-use state. The connector may be slideable with respect to the chamber when the catheter is in use so the insertion end of the catheter tube traverses the apertures of the first end wall and the second end wall of the chamber. In some instances, the connector is a cylindrical member having, in order, a first section, a second section and a third section. The first section and the third section may have an inner diameter greater than an inner diameter of the second section. In some instances, the first section seals one of the two apertures and the third section seals the second of the two apertures. In some instances, the two apertures are unsealed when the funnel is pulled through the chamber. In some instances, the system comprises a package. In some instances, the wetting device is integrated in the package.

In some instances, catheter assemblies disclosed herein comprise a sleeve that is configured to slide over the catheter. In some instances, the sleeve is an expandable sleeve, being compressed or folded before use and extended during use to be disposed around the catheter. In some instances, the sleeve is compacted in an "accordion" type configuration. In some instances, the catheter assemblies disclosed herein comprise a slidable gripper having a first gripper end connected to the second sleeve end and a free second gripper end. In some instances, the slidable gripper is disposed circumferentially around the catheter tube. The slidable gripper may be positioned and configured such that a user can pull the free second gripper end and extend the sleeve over the tube, thereby providing a means to handle the catheter tube by its sleeve versus the catheter tube itself In this way, the slidable gripper may prevent contamination of the catheter tube and an infection in the subject. The sleeve may be thin (e.g., like paper), transparent, flexible, have a good tear strength, or a combination thereof. By way of non-limiting example, the sleeve may comprise a thermoplastic elastomer. The sleeve may comprise a polyurethane. The sleeve may comprise thermoplastic polyurethane (TPU). The sleeve may comprise a polyethylene film.

Catheter tubes disclosed herein may comprise a rounded distal end that is inserted into the urethra of a user. Catheter tubes disclosed herein also comprise a proximal end with at least one aperture or opening providing for release of urine into when in use. In some instances, the catheter tube comprises a plurality of apertures or openings. In some instances, the catheter tube comprises a funnel. The funnel may comprise an elongated, substantially circular neck portion and a shoulder portion that tapers from a substantially circular configuration similar to the neck portion to a flattened, substantially oval spout. In some instances, the neck portion is elongated so that it passes completely through a wetting device sub-assembly as described herein. The neck portion of the funnel may have an opening that has a diameter slightly larger than the outside diameter of the catheter. The flattened, substantially oval spout may be configured so that it maintains a low profile. The low profile may be accommodated in an opening of a catheter case.

Catheter tubes disclosed herein may be made of a flexible material such as a thermoplastic elastomer. Thermoplastic elastomers (TPE), sometimes referred to as thermoplastic rubbers, are a class of copolymers or a physical mix of polymers (usually a plastic and a rubber) which consist of materials with both thermoplastic and elastomeric properties. Thermoplastic elastomers show advantages typical of both rubbery materials and plastic materials. The benefit of using thermoplastic elastomers is the ability to stretch to moderate elongations and return to its near original shape creating a longer life and better physical range than other materials. Alternative materials for catheter tubes disclosed herein include polyvinyl chlorides (PVC) or rubber. Other alternative materials include those described in U.S. Pat. No.

9,186,438, which is incorporated by reference in its entirety herein. This patent describes polymer mixtures comprising a first and a second polymer, with the first polymer being a thermoplastic or thermo-curing polymer and the second.

In some embodiments, a catheter tube comprises or is integrated with a polymer, such as a hydrophilic polymer. In some embodiments, the catheter tube is coated with a polymer, such as a hydrophilic polymer. In some embodiments, the catheter tube comprises or is integrated with a polymer mixture of a thermoplastic or thermo-curing polymer base material and an amphiphilic block copolymer, e.g., as disclosed in WO 2011/051439 filed Oct. 29, 2010, the entirety of which is incorporated by reference herein. In some embodiments, the catheter tube is coated with the polymer mixture of a thermoplastic or thermos-curing polymer base material and amphiphilic block copolymer, e.g., as disclosed in WO 2011/051439.

In some instances, catheter assemblies disclosed herein comprise a funnel, wherein at least a portion of the funnel is dumbbell-shaped. In some instances, funnels have a dumbbell-shaped neck portion that includes an enlarged diameter distal end, i.e., the end disposed toward the catheter, gradually tapering to a relatively reduced diameter at the proximal end, i.e., the end disposed away from the catheter. The distal end of the funnel may have an enlarged internal diameter sized and configured to accommodate the outer diameter of the catheter. The catheter and distal end can be connected at the junction of internal diameter and outer diameter by, e.g., an adhesive or by welding. A non-limiting example of a suitable adhesive is a UV-curable adhesive. The inside diameter of the remainder of the dumbbell-shaped neck portion may be substantially the same as the inside diameter of the catheter. The funnel may have a distal terminal end having an internal size that is configured to engage with a gradually tapering proximal end. The funnel may have a substantially circular central portion that is connected to a shoulder portion that tapers from a substantially circular configuration to a flattened, substantially oval spout. The central portion also may have an internal diameter (not shown) that is substantially the same as at least one internal diameter. The funnel may have a substantially oval spout that is configured so that it maintains a low profile accommodating a low-profile catheter case. In some instances, the cross-sectional area of the substantially oval spout is the same as or greater than the cross-sectional area of internal diameters for the same reason. These relative diameters may allow for a smoother flow, and reduced possibility of "backup", of urine through the catheter or funnel.

Provided are methods of using catheter assemblies disclosed herein. Methods may comprise inserting a urinary catheter of the present disclosure into the urethra. Methods may comprise probing for the urethra with a catheter tube having a locator tip of the present disclosure. Methods may comprise inserting a urinary catheter into the urethra, wherein the locator tip does not enter the urethra. In some instances, methods comprise removing a cap from the catheter tube before use, wherein the cap covers the locator tip. In some instances, methods comprise moving a cap that covers the locator tip in order to expose the locator tip. Methods may comprise fixing the cap to an end of the catheter tube after use.

EXAMPLES

Referring to FIG. 1, catheter assemblies disclosed herein may be configured in a small, compact case 100. The case may generally have an outer body 102 and a cap 104 proximal the distal tip of the catheter tube. The case may have a distal end 106 and a proximal end 108 that is pushed in the direction of cap 104 after the cap is removed in order to move the catheter tube through a locator tip near the distal tip of the catheter tube.

Figure 2:
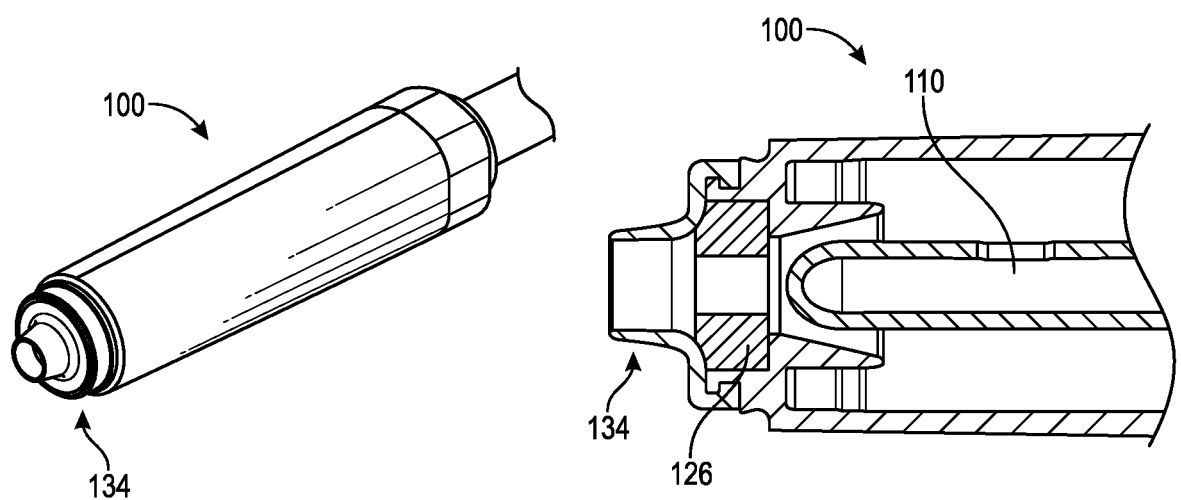
FIG. 2 shows an exemplary female urinary catheter, with a cap removed, exposing a locator tip on the distal end of the female urinary catheter (outer view left, side view cross section right).

FIG. 2 shows an outer view of a catheter assembly 100 and a side view of a cross-section of a catheter assembly 100. On the left, the catheter assembly 100 is shown with cap (not shown) removed to expose the locator tip 134. Locator tip 134 may be described as tapered, with a slope that may gradually increase to the base of the locator tip. Locator tip 134 may be described as cone shaped. Although hollow, the locator tip 134 may be described as having a flat end. Locator tip 134 may be described as having a blunt end. The locator tip end has a diameter that is smaller than the base of the locator tip where it is attached to the device housing. A cross-sectional side view depicts the catheter tube 110 protected from exposure by the locator tip 134. In addition, in this exemplary case, the catheter tube 110 must be pushed through a wetting device 126 and the locator tip 134 before it will make contact with tissue.

Figure 3:
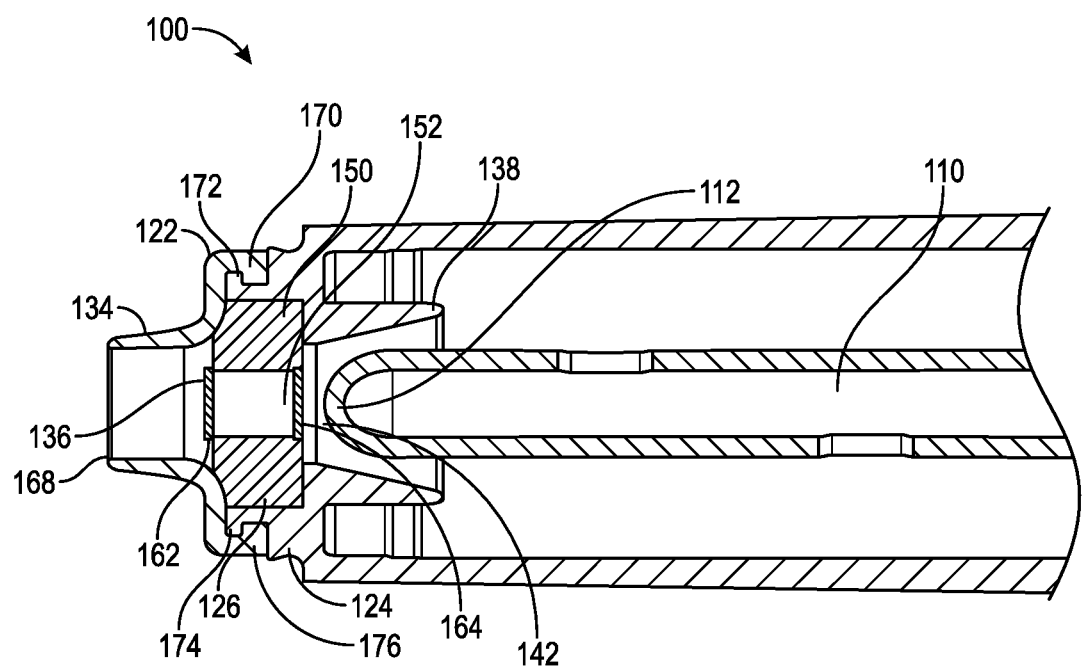
FIG. 3 shows a side view cross section of an exemplary female urinary catheter comprising a locator tip where the cap (not shown) has been removed.

FIG. 3 shows an additional side view of a cross-section of a catheter assembly 100 comprising a catheter tube 110 having a distal tip 112; an elongated portion 138 that may guide the path of the catheter tube; wetting applicator 150 with a connector 152 disposed therethrough; a housing lip 172, 174 and a locator tip ring 170, 176 that attach the locator tip to the housing. The connector may have plugs 162 and 164 to maintain a seal to the wetting agent in the wetting applicator 150. The locator tip may have a tapered region 134 near the locator tip opening 168. The wetting device 126 may comprise a chamber formed by a rearward section 124 and a forward section comprising locator tip 122. Wetting device 126 may have an opening 136 through the forward section and a housing opening 142 through rearward section 124. These openings 136, 142 may be disposed in concentric alignment with catheter tube 110 so that the catheter can be pushed through the wetting device 126 along a central axis thereof. In general, the catheter tube 110 will move through the housing opening 142, to be wetted by the wetting applicator 150, moving beyond through the locator tip end 134 after the urethra is located by the locator tip 122.

Figure 4:
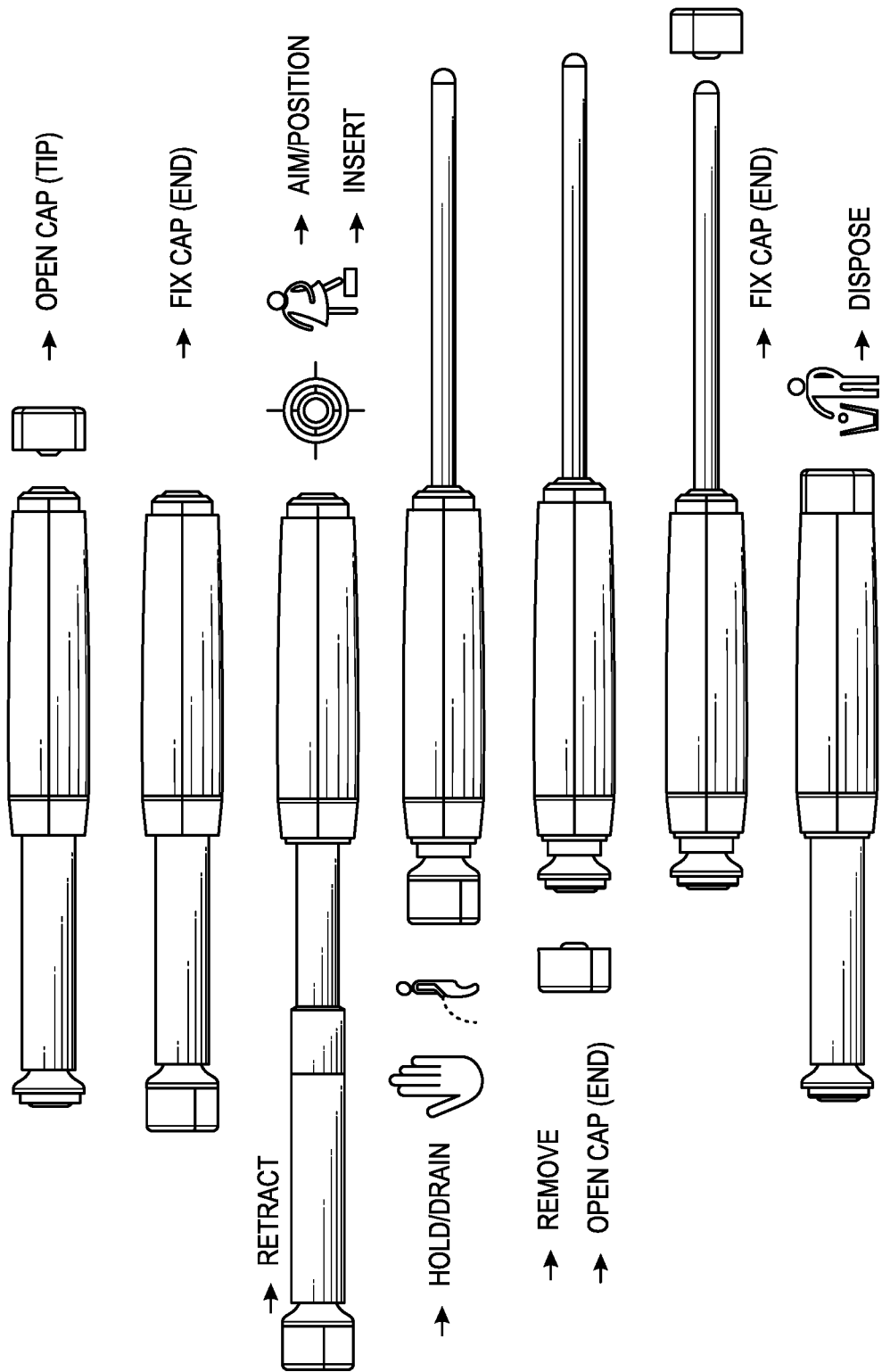
FIG. 4 shows an exemplary sequence of using a female catheter with a locator tip.

FIG. 4 shows a sequence of events during use of a catheter assembly disclosed herein from top to bottom. First, a cap may be removed from the distal end of the device to reveal the locator tip. The cap may be pulled off or twisted off. Next, the cap may be fixed to the proximal end of the catheter assembly. An actuator is retracted and the locator tip is used to target the urethra. Once the urethra is found, the actuator is pushed through the catheter housing and through the locator tip. The user may then relieve themselves of urine. The cap may be removed before or after relieving. The cap may be used to push the catheter tube back into the housing before disposal.

Figure 5:
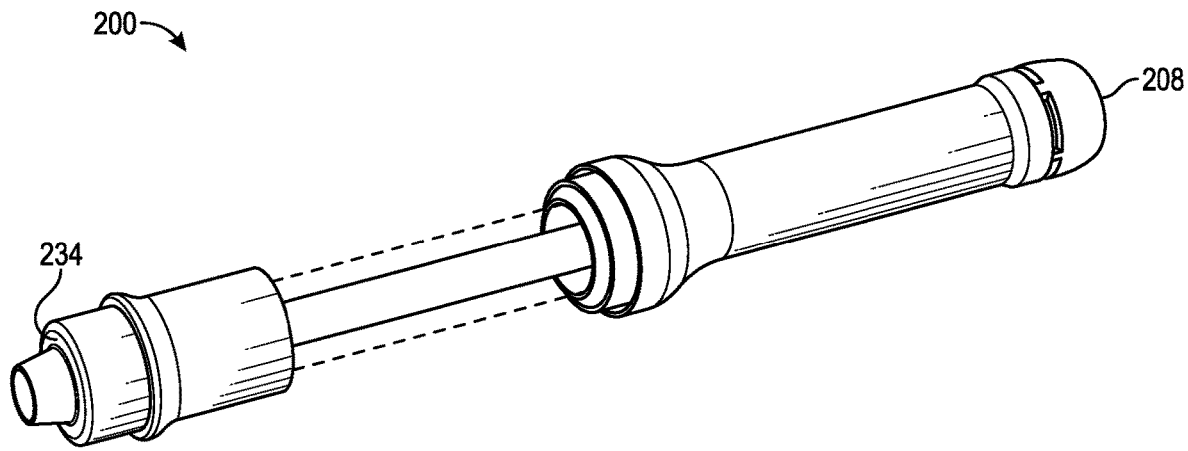
FIG. 5 shows an exemplary perspective of a female catheter device with a locator tip in a position for targeting a urethra, but before insertion.

FIG. 5 shows female urethral catheter system 200 prior to insertion of the urethral catheter tube (not shown) into the subject. The female catheter system includes a proximal end 208 and a locator tip 234 on a distal portion of the catheter system 200. The catheter system in FIG. 5 may be an alternative to those of FIGS. 1-4.

Figure 6:
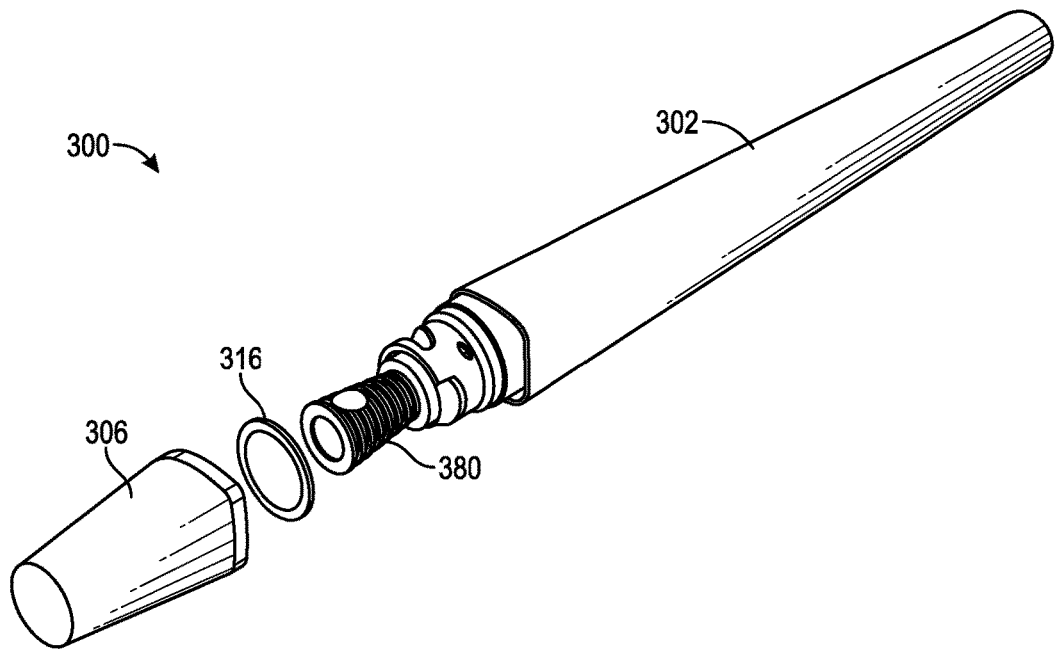
FIG. 6 shows an exploded view of the cap portion of an additional female urinary catheter as packaged.
Figure 7:
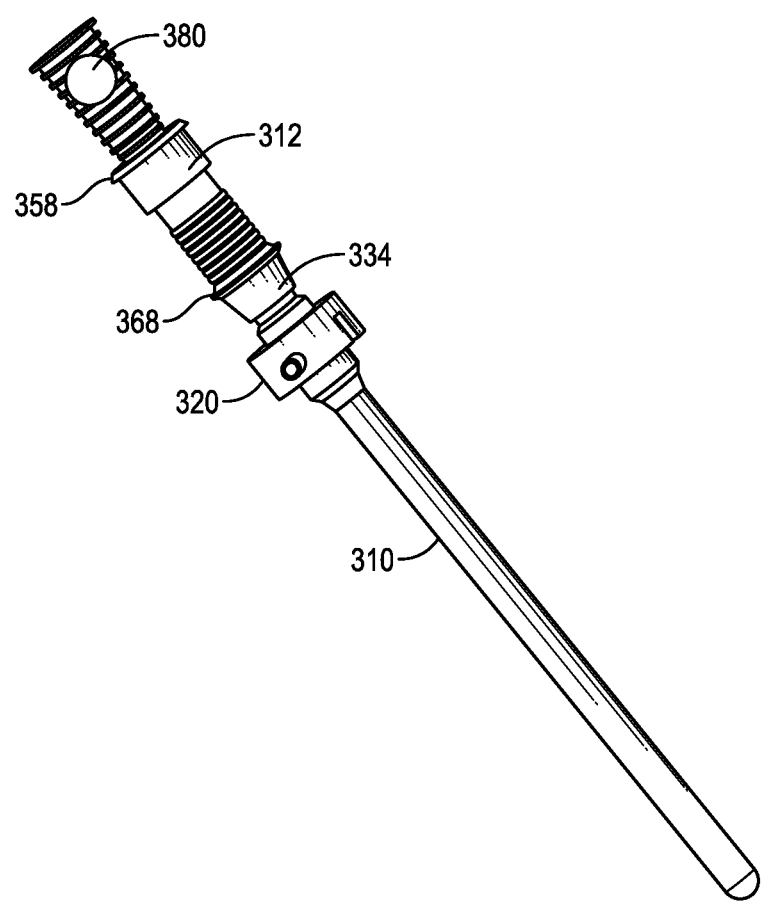
FIG. 7 shows an exemplary female urinary catheter comprising a wetting device and locator tip, shown without its case or housing, but as it would appear before removing it from the case or housing. With its case or housing, it may appear as in FIG. 6.
Figure 8:
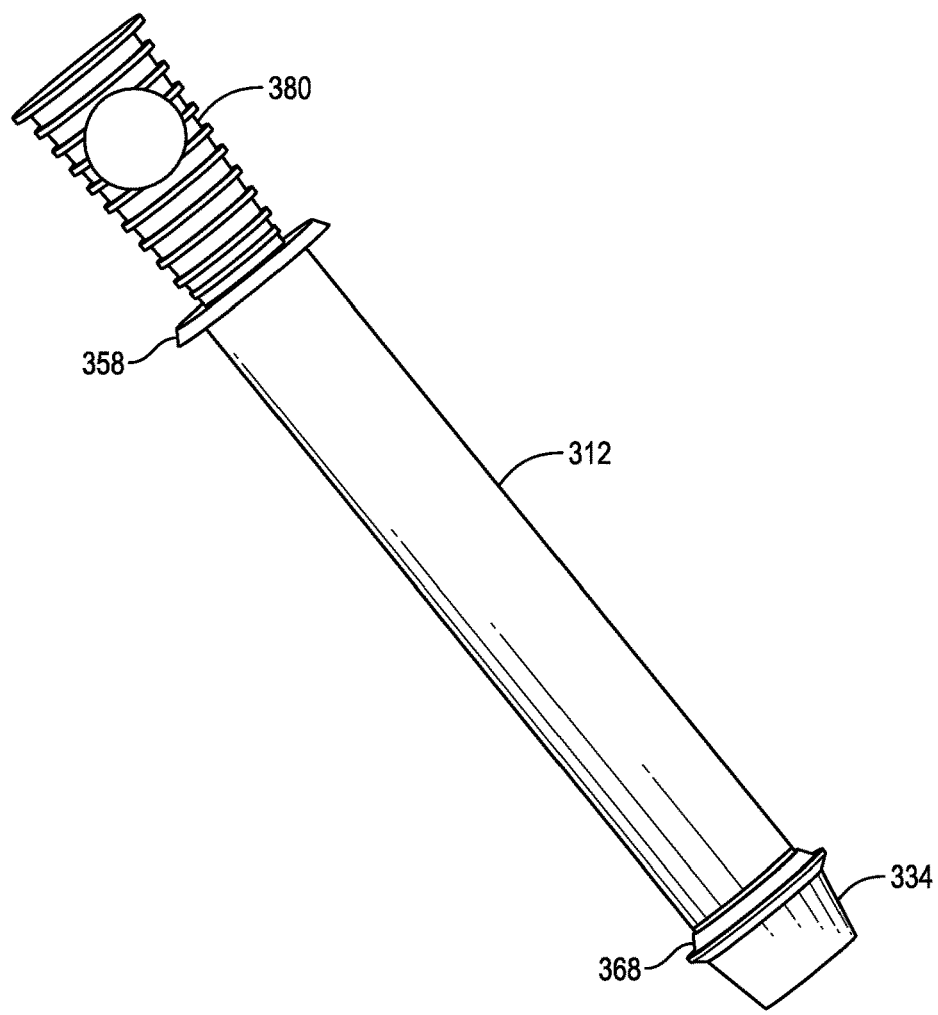
FIG. 8 shows an exemplary female urinary catheter comprising a locator tip in an extended state, as it would appear after extending a sleeve and locator tip over the catheter tube.

Referring to FIGS. 6-8, catheter assemblies may alternatively be packaged in a small and compact device that keeps the catheter tube sterile until use. FIG. 6 shows an exploded view of a cap of a catheter assembly 300, having a case containing a female urinary catheter with a locator tip. The case has a lid 306, a seal 316 and a catheter tube housing 302. The seal 316 may be an O-ring. When lid 306 is removed upon use, funnel 380 is exposed. The user may withdraw the catheter tube from the catheter tube housing 302, where it will appear as shown in FIG. 7. After use, the catheter tube may be reinserted into the catheter tube housing 302, and the lid 306 replaced. The seal 316 is intended to prevent any fluids from leaking until disposal of the assembly.

FIG. 7 shows a catheter tube assembly prior to use, with catheter tube 310 and funnel 380, where the catheter tube 310 is uncovered. A locator tip 334 and concertina or accordion sleeve assembly 312 may be located at the proximal portion of the catheter tube assembly. This figure may aid the viewer in understanding how the internal contents of the catheter assembly in FIG. 6 may appear. When removed from a case, wetting device 320 would remain in the case, the catheter tube 310 being drawn through the wetting device 320 to be wetted as the catheter tube assembly is withdrawn from the case. A gripper 358 may be attached to the funnel 380, and serve as a means to withdraw the catheter from its case, as well as a means to hold the catheter, with locator tip base 368, when extending sleeve 312 over the catheter tube.

FIG. 8 shows the catheter tube upon removal from the case and in an extended state, where sleeve 312, together with locator tip 334, are drawn over catheter tube 310 to the distal end of the catheter tube 310. In some instances, sleeve 312 is connected to locator tip 334 directly or indirectly. In some instances, sleeve 312 is connected to locator tip 334 via locator tip base 368.

Figure 9:
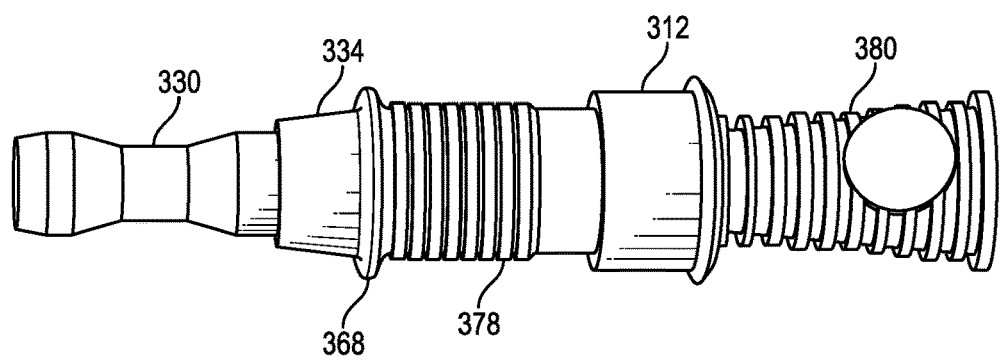
FIG. 9 shows an exemplary female urinary catheter comprising a locator tip in a retracted state.

FIG. 9 shows a detailed view of the proximal end of a catheter assembly, such as that shown in FIG. 7. However, this view does not show a wetting device enclosure. Instead it shows a connector 330 that is capable of moving through a wetting device, and connects catheter tube 310 (not shown) and funnel assembly 380. The connector 330 is typically connected to the catheter tube. The connector 330 may have a dumbbell appearance, the wider ends applying pressure to a wetting applicator in a wetting device to release wetting agent on to a catheter tube as it follows the connector 330 through the wetting device. Thus, according to this figure, a user would grab funnel 380 and pull the catheter tube assembly, including connector 330 and catheter tube (not shown) out of the case. As the catheter tube assembly is removed from the case, the catheter tube is wetted with wetting agent and sleeve 312 is drawn over the connector 330 and catheter tube simultaneously or substantially simultaneously, see for example, FIG. 8. After the catheter tube is removed from the case and wetting device, the user may continue to hold sleeve 312, locator tip base 368 and locator tip grip 378 covered by sleeve 312. In some instances, the user may with their other hand guide locator tip to the urethra, meanwhile keeping the catheter tube sterile. Once the urethra is located, the user puts force on the funnel 380 to move it towards the locator tip, thereby moving the catheter tube through the locator tip and into the urethra.

What is claimed is:

1. An apparatus, comprising: a catheter assembly comprising:
    a catheter tube including a distal tip configured for insertion into a female urethra;
    a locator tip including: a tubular portion; and
    a sleeve coupled to the locator tip; and
    a case for storing the catheter assembly;
    wherein the sleeve is configured to extend over and along the catheter tube during removal of the catheter assembly from the case;
    wherein removal of the catheter assembly from the case causes the sleeve to transition from the contracted state to the elongated state, thereby causing the sleeve to extend along the catheter tube.

2. The apparatus of claim 1, further wherein the locator tip is disengaged from the case when the distal end of the catheter assembly is removed from the case.

3. The apparatus of claim 1, further wherein the sleeve is connected to the locator tip.

4. The apparatus of claim 1, further comprising a wetting device configured to wet the catheter tube with a wetting agent upon removal of the catheter assembly from the case.

5. The apparatus of claim 1, wherein the sleeve is configured to transition from a contracted state to an elongated state as a result of removal of the catheter assembly from the case.

6. An apparatus, comprising:
    a case; and
    a catheter assembly received in the case, the catheter assembly comprising:
        a sleeve having a contracted state and an elongated state;
        a locator tip mounted to an end of the sleeve; and
        a catheter tube comprising a distal tip configured for insertion into a female urethra;
    wherein removal of the catheter assembly from the case causes the sleeve to transition from the contracted state to the elongated state, thereby causing the sleeve to extend along the catheter tube; and
    wherein the catheter tube is operable to pass through the locator tip.

7. The apparatus of claim 6, wherein:
    the locator tip appears conical from a side view of the catheter assembly; or
    the locator tip appears rounded from a side view of the catheter assembly; or
    the locator tip appears circular from an end view of the catheter assembly.

8. The apparatus of claim 6,
    wherein the locator tip is characterized by a height that is parallel with a length of the catheter tube and a width that is perpendicular to the length of the catheter tube when the catheter tube is extended; and
    wherein:
        the width is not less than 2 cm; or
        the width is not less than 1.5 cm; or
        the width is not less than 1 cm.

9. The apparatus of claim 6,
    wherein the locator tip is characterized by a height that is parallel with the length of the catheter tube and a width that is perpendicular to the length of the catheter tube when the catheter tube is extended; and
    wherein the height is not greater than 1 cm.

10. The apparatus of claim 6, further wherein the sleeve is configured to be held by the user as the urethra is being located.

11. The apparatus of claim 6, further comprising a cap, configured to cover at least a portion of the catheter assembly until use.

12. The apparatus of claim 11, wherein the cap is also configured to cover a catheter tube proximal opening.

13. The apparatus of claim 12, wherein the catheter tube comprises a funnel and the cap is also configured to cover the funnel.

14. The apparatus of claim 6, wherein the sleeve is compacted prior to use.

15. The apparatus of claim 14, wherein the sleeve and locator tip are compacted in a proximal region of the catheter assembly prior to use.

16. A method for using a catheter assembly, comprising:
   providing the catheter assembly of claim 6;
   probing tissue around a female urethra with the locator tip; and
   inserting the catheter tube into the urethra,
   wherein the locator tip is not inserted into the urethra.

17. The method of claim 16, further comprising holding the sleeve as the urethra is being located.

18. The apparatus of claim 6, wherein the locator tip comprises a tubular portion.

19. The apparatus of claim 6, wherein the locator tip is initially received in the case, and is configured to move out of the case when a distal end of the catheter assembly is removed from the case.

20. The apparatus of claim 6, wherein the sleeve is configured to extend over the catheter tube upon removal of the catheter assembly from the case.

* * * * *